United States Patent [19]

Everhart et al.

[11] Patent Number: 4,578,531

[45] Date of Patent: Mar. 25, 1986

[54] ENCRYPTION SYSTEM KEY DISTRIBUTION METHOD AND APPARATUS

[75] Inventors: Joseph R. Everhart, Holmdel; Jeffrey G. Osborn, Old Bridge, both of N.J.

[73] Assignee: AT&T Bell Laboratories, Murray Hill, N.J.

[21] Appl. No.: 386,805

[22] Filed: Jun. 9, 1982

[51] Int. Cl.⁴ .............................................. H04K 1/02
[52] U.S. Cl. .............................. 178/22.08; 178/22.11
[58] Field of Search ................ 178/22.07, 22.11, 22.08

[56] References Cited

U.S. PATENT DOCUMENTS

| | | | |
|---|---|---|---|
| 4,182,933 | 1/1980 | Rosenblum | 178/22.04 |
| 4,200,770 | 4/1980 | Hellman et al. | 178/22.11 |
| 4,203,166 | 5/1980 | Ehrsam et al. | 178/22.07 |
| 4,218,738 | 8/1980 | Matyas et al. | 178/22.08 |
| 4,238,853 | 12/1980 | Ehrsam et al. | 178/22.09 |
| 4,386,233 | 5/1983 | Smid et al. | 178/22.14 |
| 4,417,338 | 11/1983 | Darida | 178/22.09 |
| 4,418,275 | 11/1983 | Oosterbaan et al. | 178/22.14 |

Primary Examiner—Salvatore Cangialosi
Attorney, Agent, or Firm—David H. Tannenbaum

[57] ABSTRACT

Encryption systems typically rely on the distribution of cipher keys between terminals for scrambling and unscrambling transmitted messages. Elaborate security precautions are necessary to protect the cipher keys since a compromise of the key could result in a compromise of the transmission. There is disclosed a key distribution method and apparatus which uses a channel from identified terminals to a central key distribution center for the establishment, on a one-session basis, of the key which is to be used for the next session between those terminals. The key establishing link is itself encoded using a cipher key which changes after each usage. Provision is made to verify, for each new connection, that a compromise has not priorly occurred.

18 Claims, 28 Drawing Figures

KDC CONFIGURATION

INITIAL SYSTEM SETUP

TERMINAL A

TERMINAL A

KDC

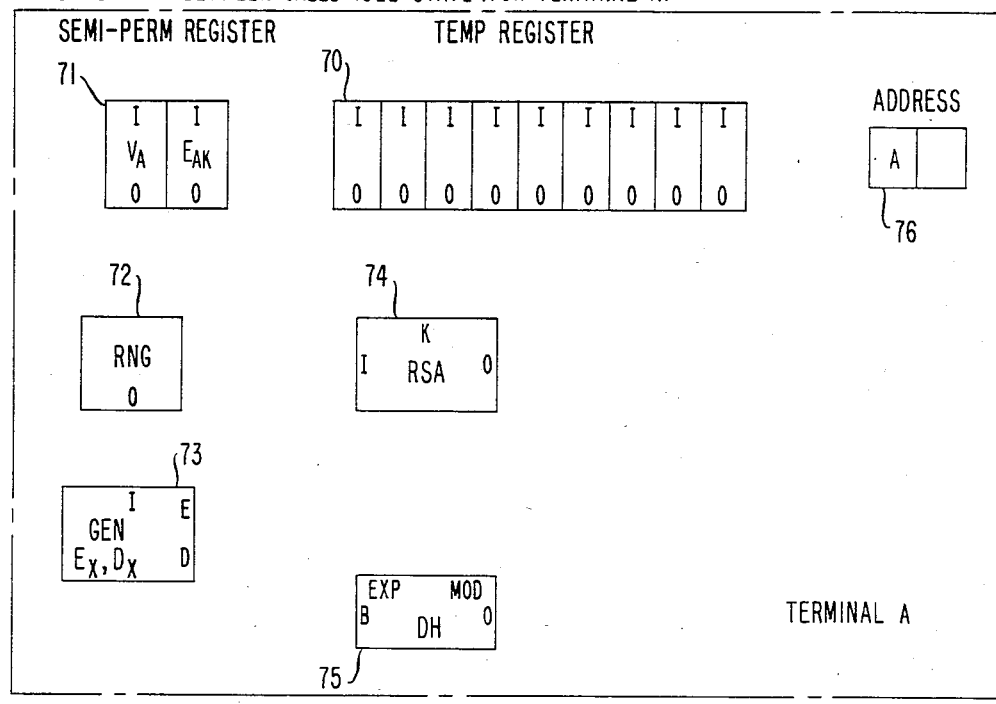
FIG. 6    BETWEEN CALLS IDLE STATE (FOR TERMINAL A)
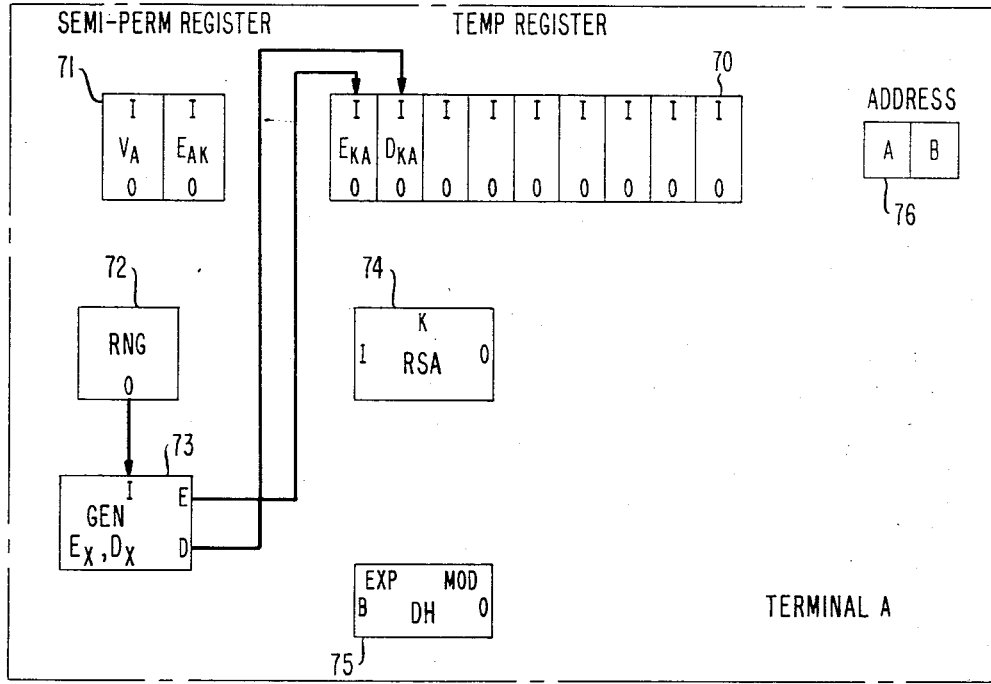
FIG. 7    START OF SECURE CALL (A TO B) SETUP - GENERATION OF KDC-A LINK KEYS

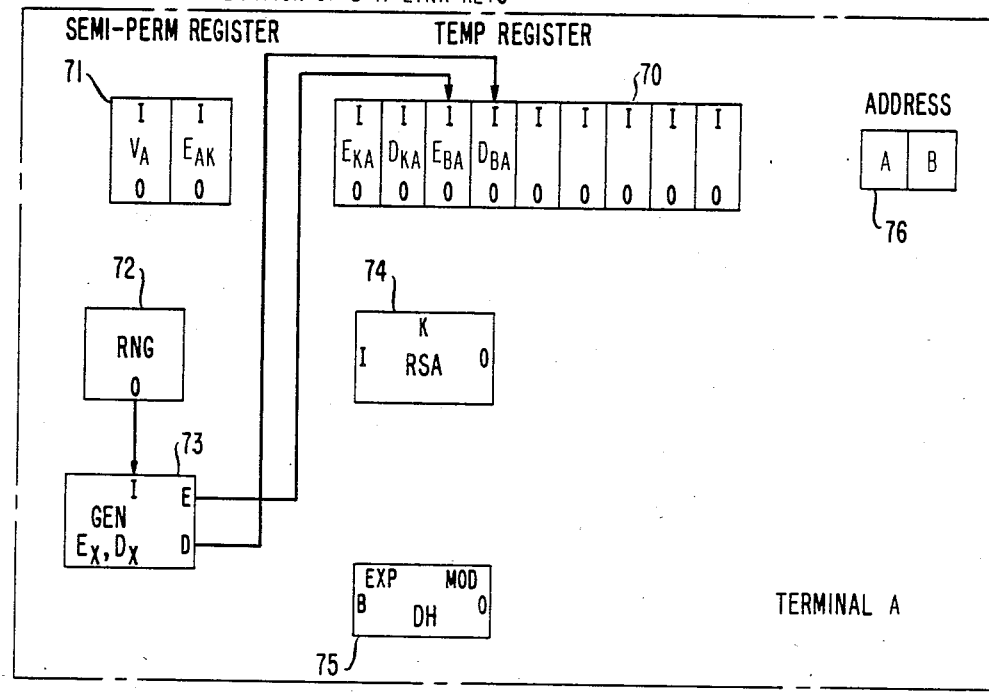
FIG. 8  GENERATION OF B-A LINK KEYS
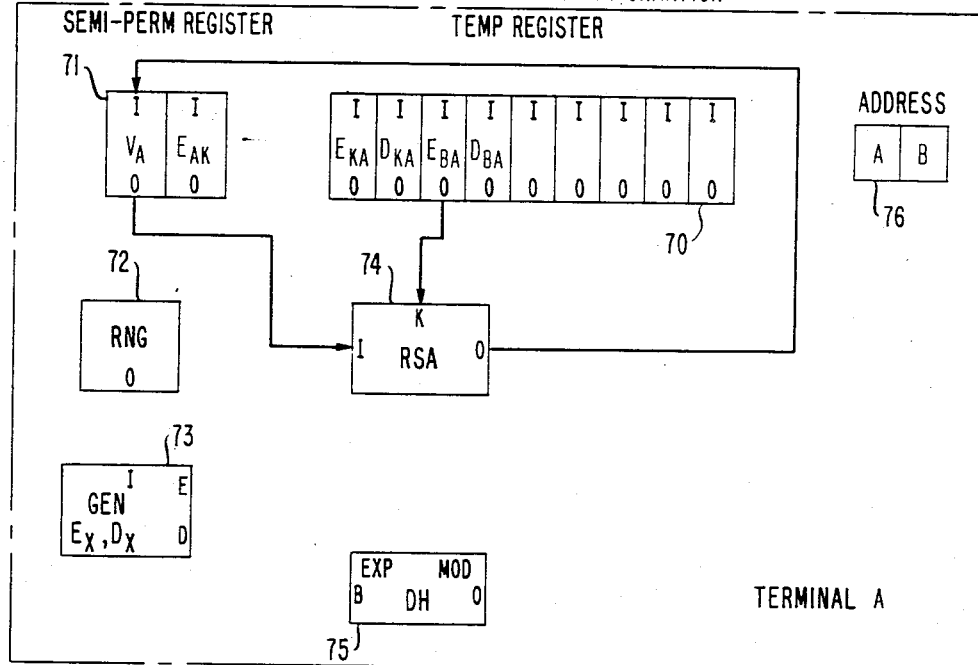
FIG. 9  FIRST STEP IN UPDATE OF VERIFICATION INFORMATION

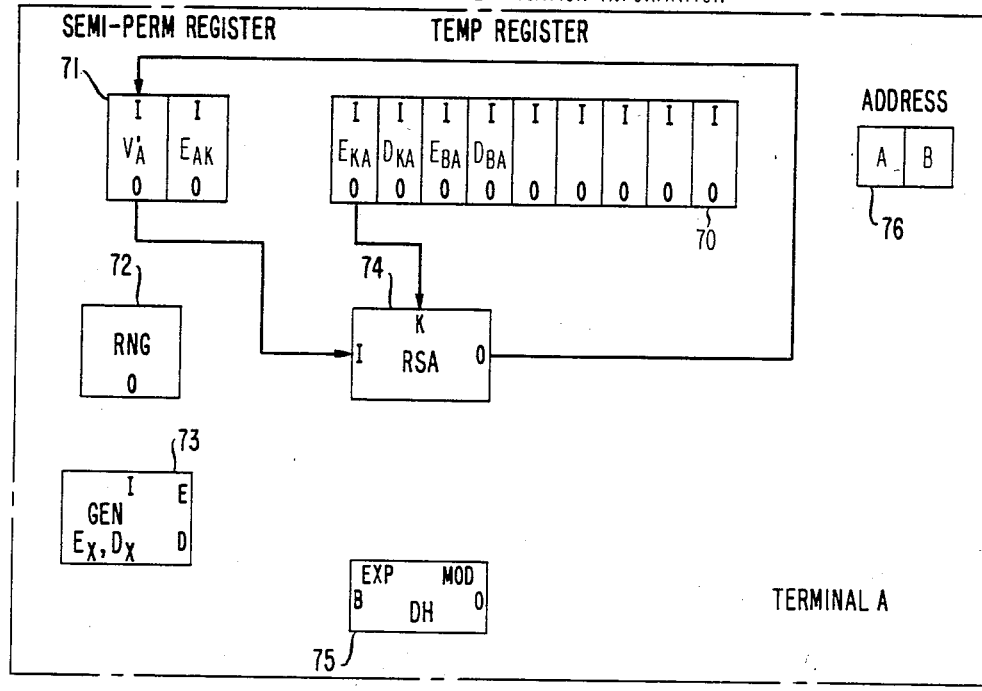
FIG. 10 SECOND STEP IN UPDATE OF VERIFICATION INFORMATION
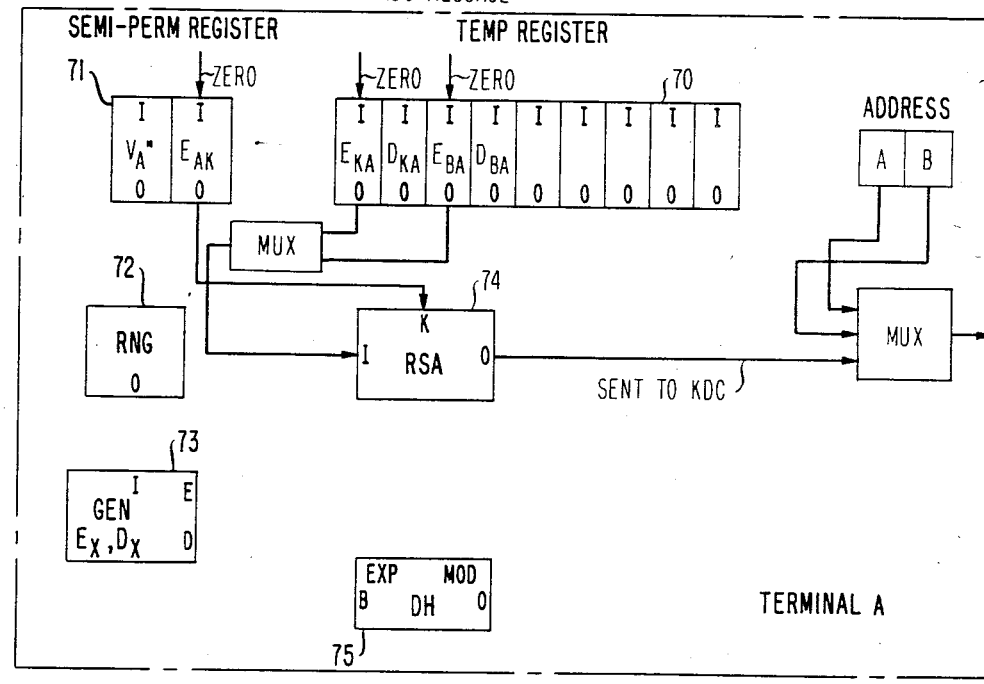
FIG. 11 COMPUTATION OF A-KDC MESSAGE

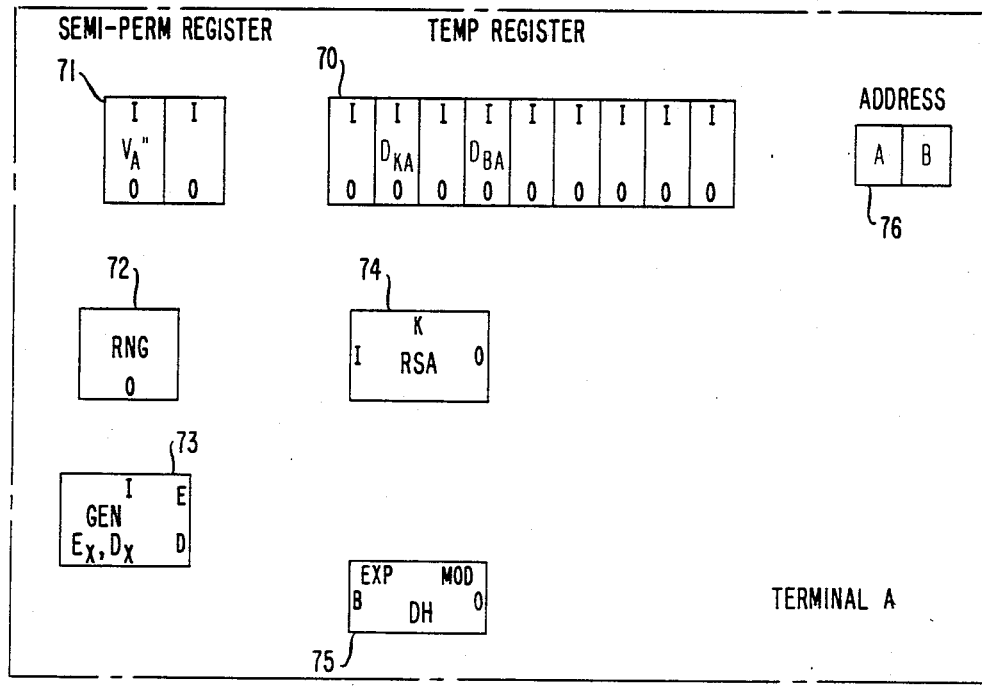
FIG. 12  IDLE STATE WHILE WAITING FOR RETURN MESSAGE FROM KDC
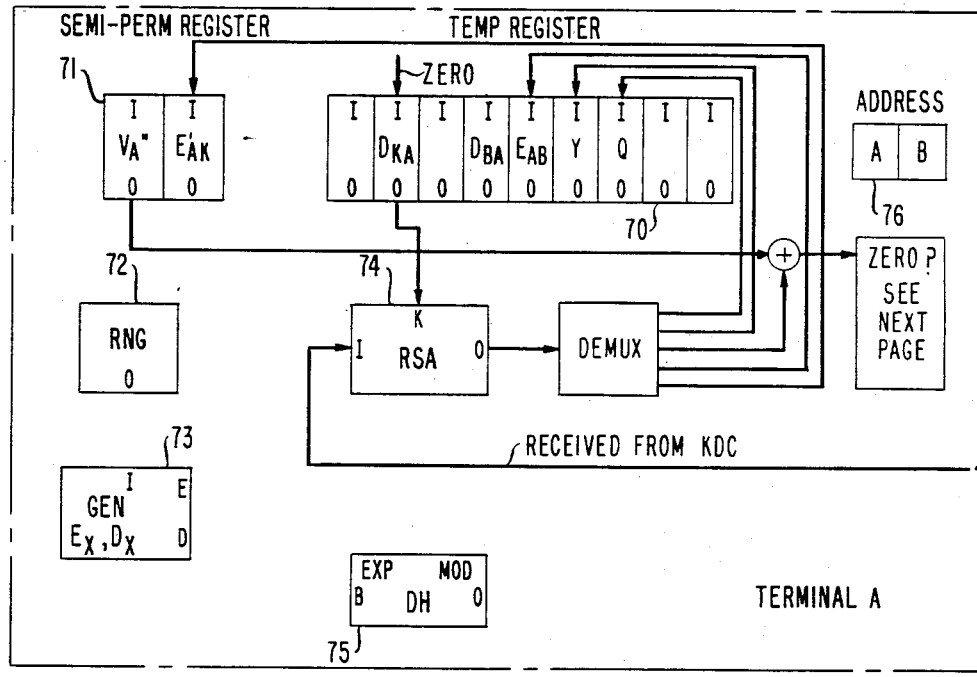
FIG. 13  DECRYPTION OF RETURN MESSAGE FROM KDC

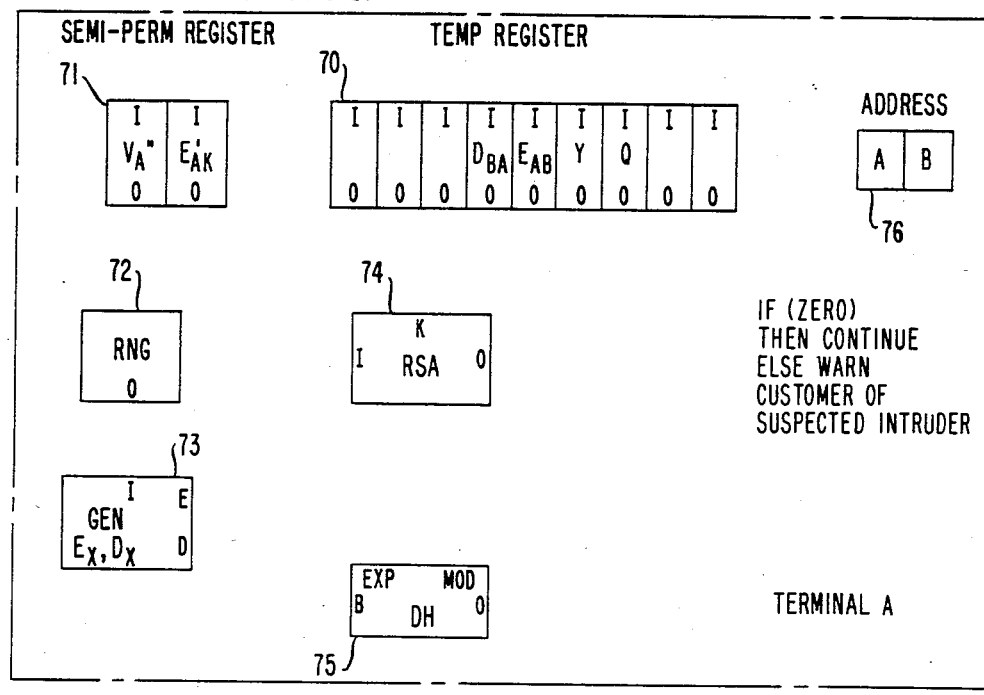
FIG. 14 VERIFICATION CHECK
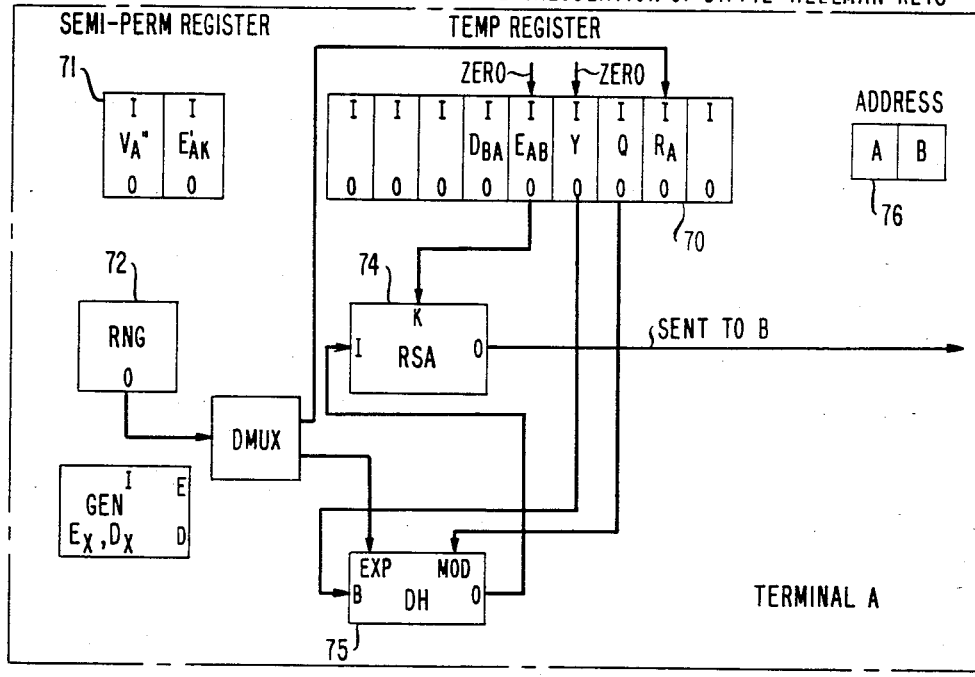
FIG. 15 START OF KEY EXCHANGE WITH B CALCULATION OF DIFFIE-HELLMAN KEYS

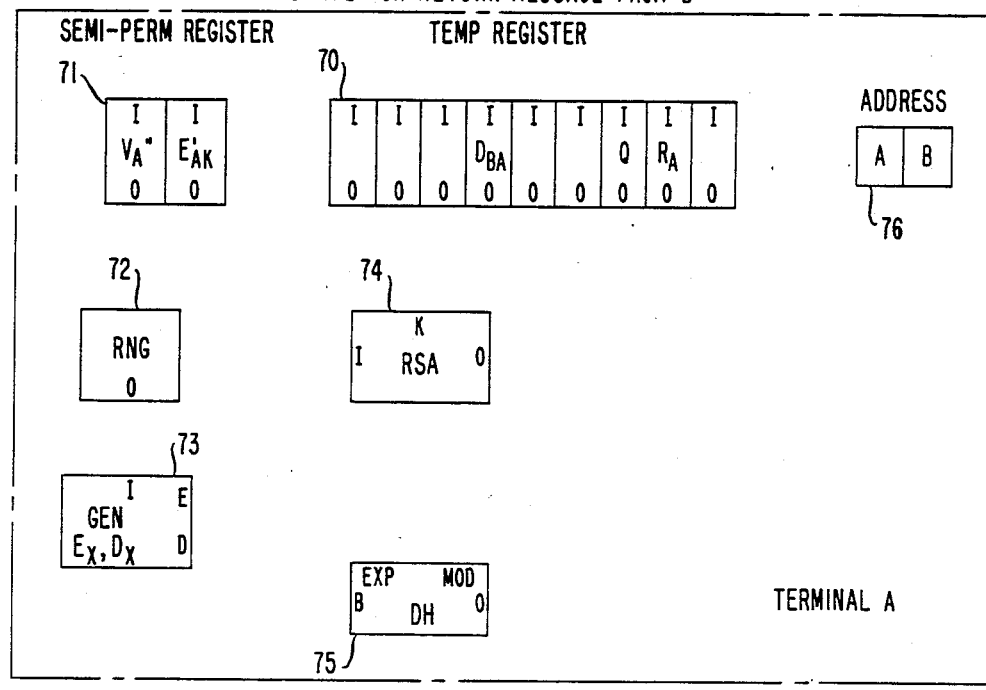
FIG. 16  IDLE WAIT STATE FOR RETURN MESSAGE FROM B
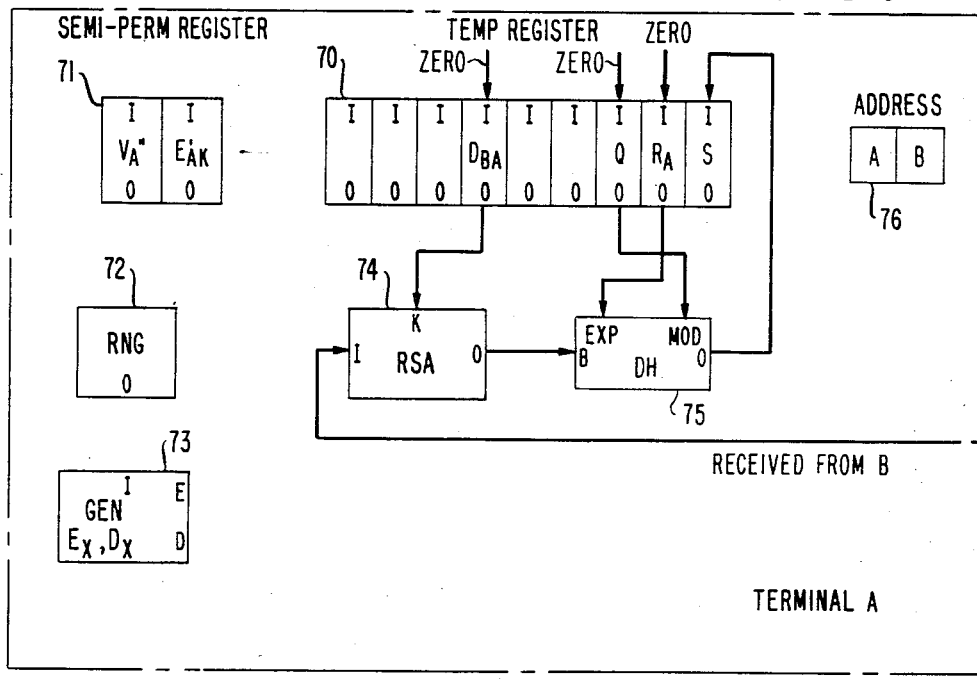
FIG. 17  DECRYPTION OF MESSAGE FROM B AND CALCULATION OF SESSION KEY-S

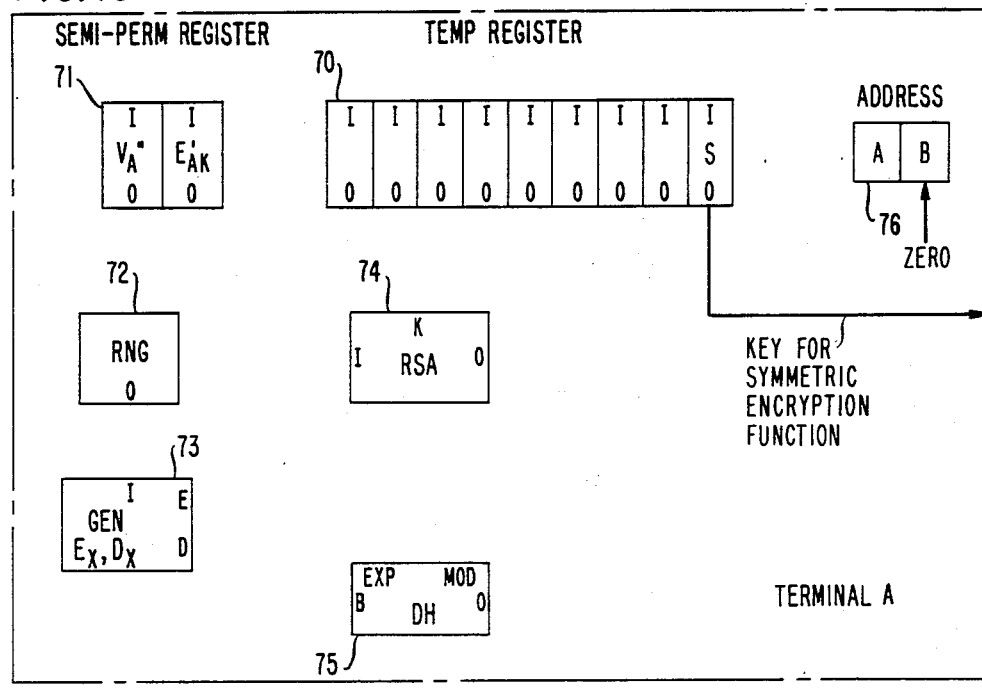
FIG. 18 KEY STORAGE DURING CALL
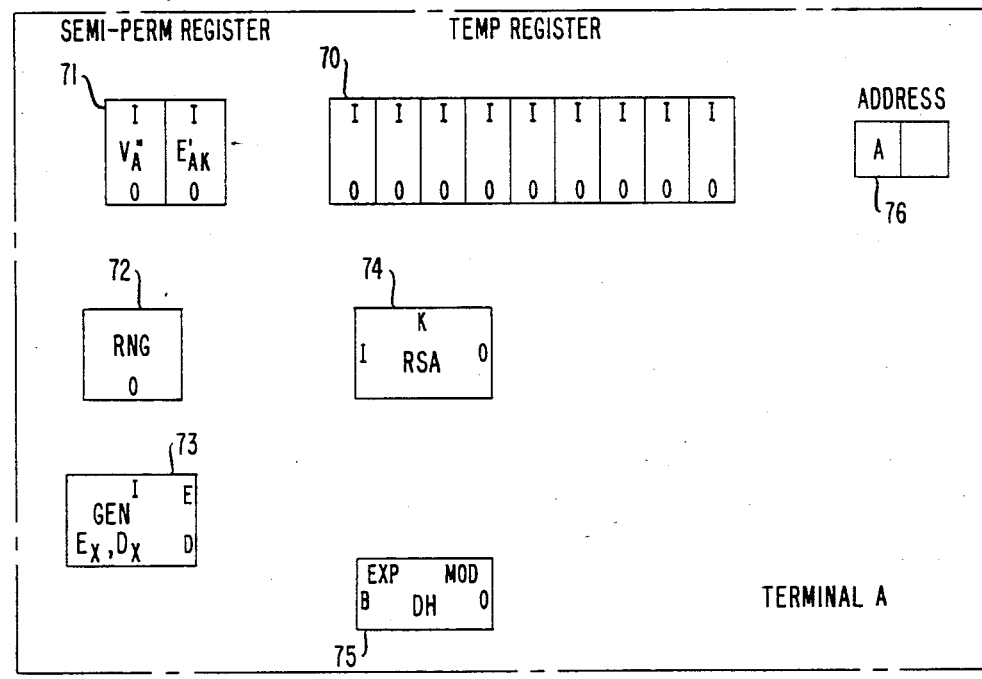
FIG. 19 IDLE STATE FOLLOWING CALL COMPLETION

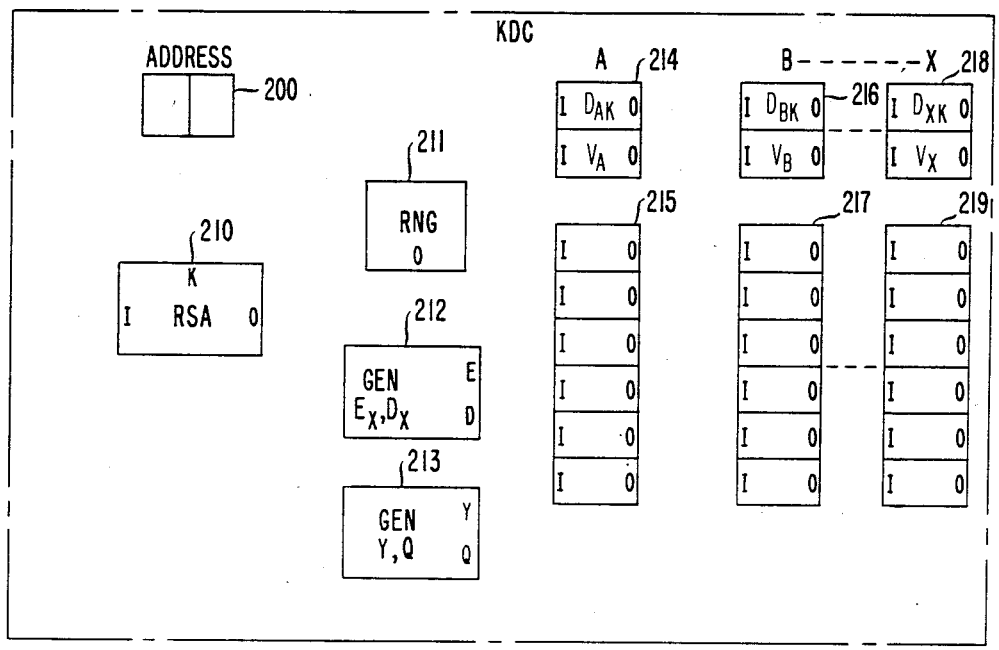
FIG. 20 IDLE STATE BETWEEN CALLS
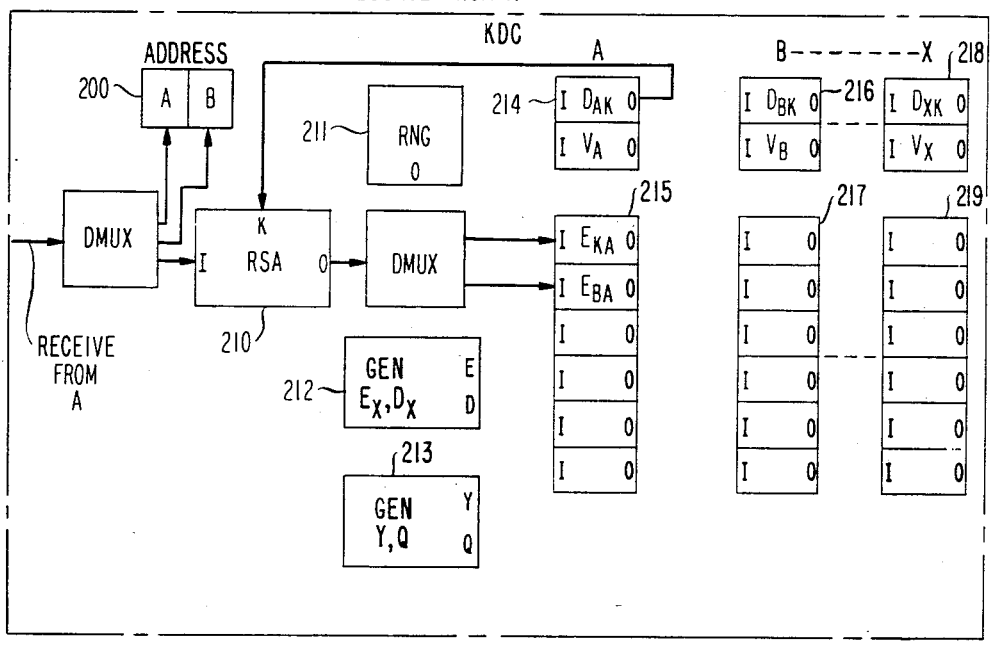
FIG. 21 DECRYPTION OF MESSAGE FROM A FIG. 22 FIRST STEP IN THE UPDATE OF VERIFICATION INFORMATION
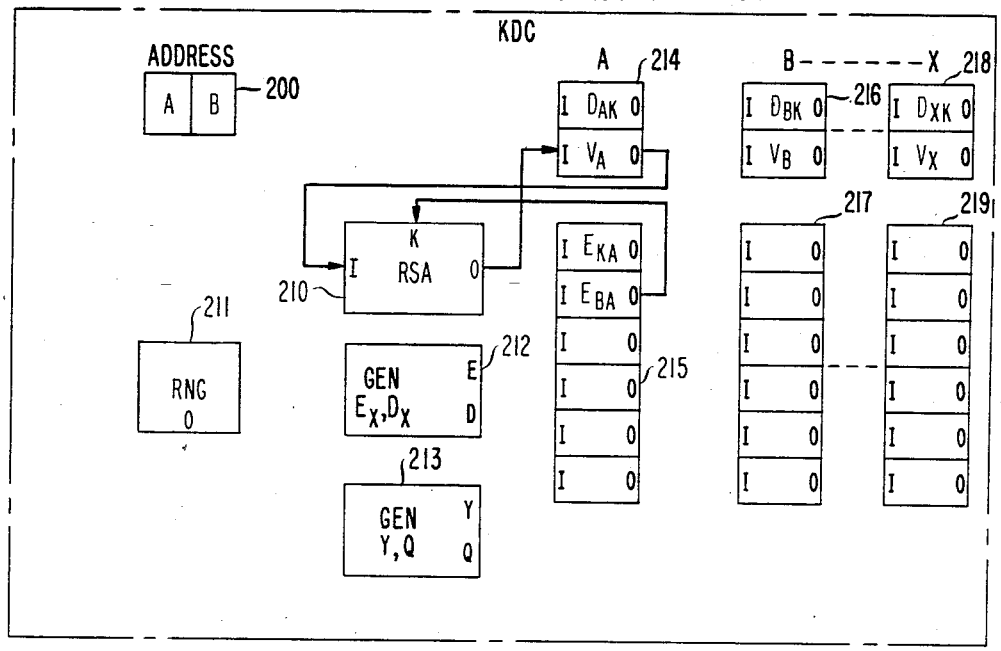
FIG. 23 SECOND STEP IN THE UPDATE OF VERIFICATION INFORMATION
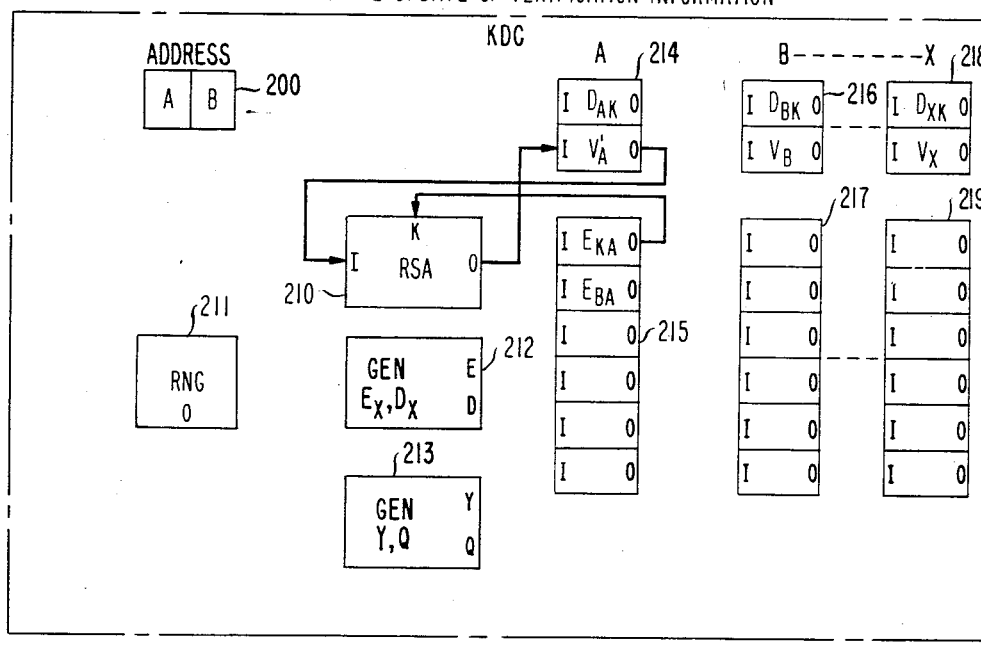

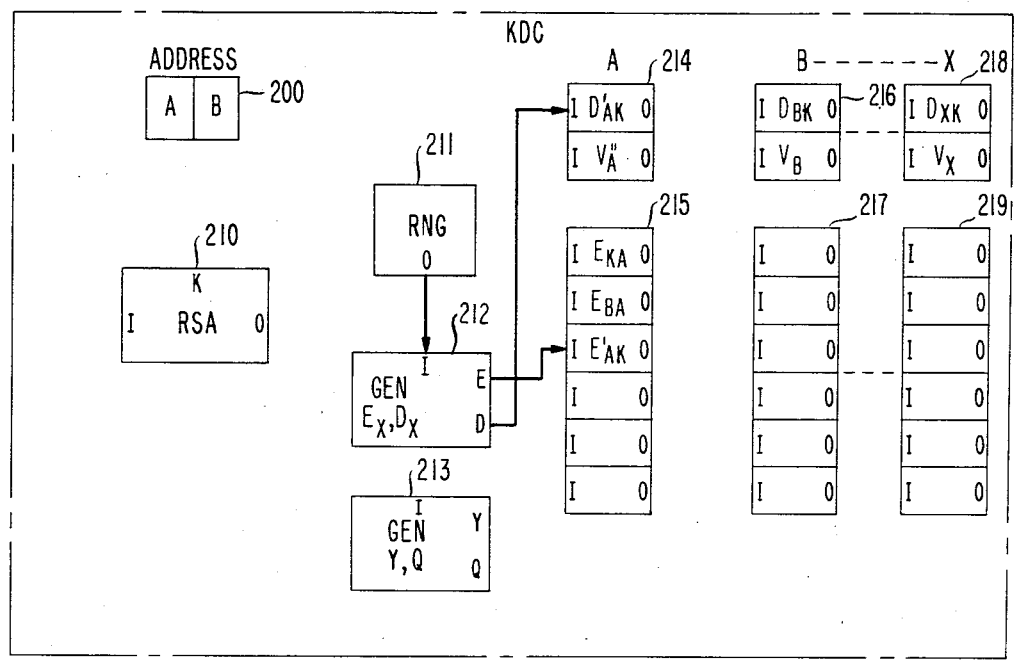
FIG. 24  GENERATION OF NEW KDC-A LINK KEYS
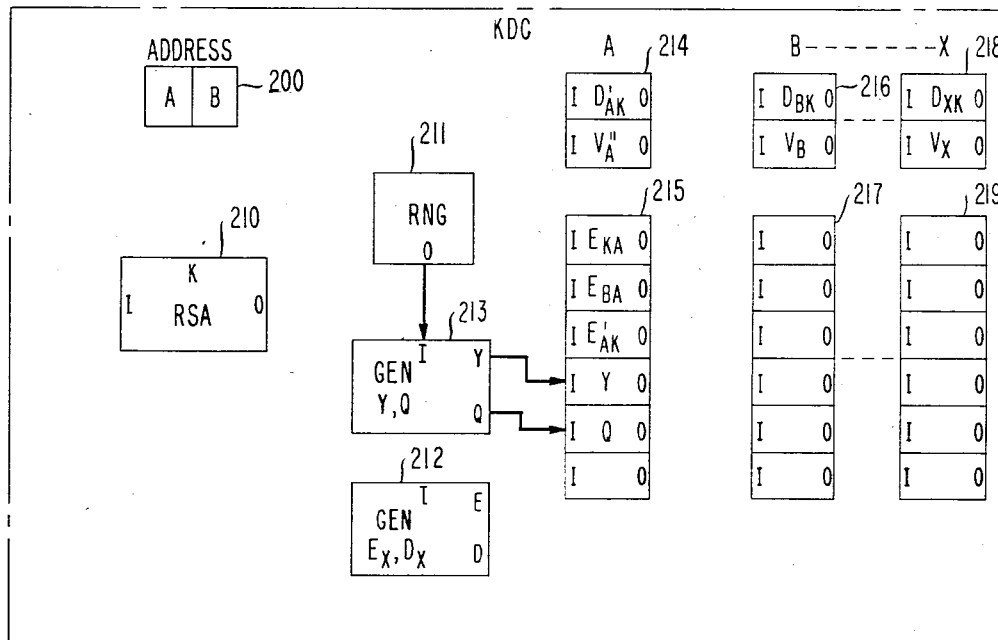
FIG. 25  GENERATION OF DIFFIE-HELLMAN ALGORITHM PARAMETERS

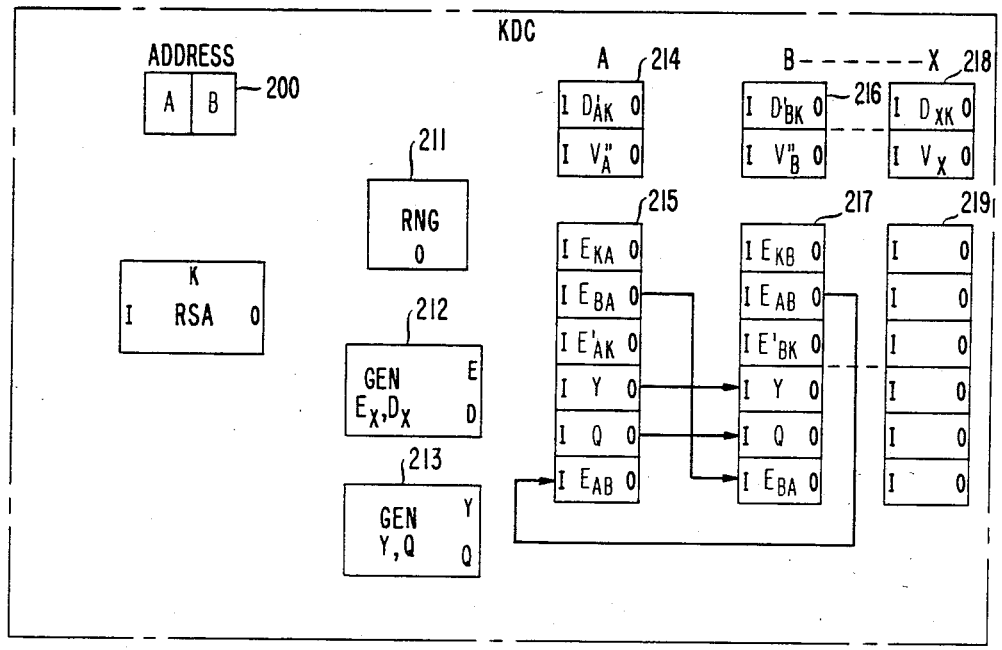
*FIG. 26* INTERNAL EXCHANGE OF INFORMATION BETWEEN A & B'S REGISTERS
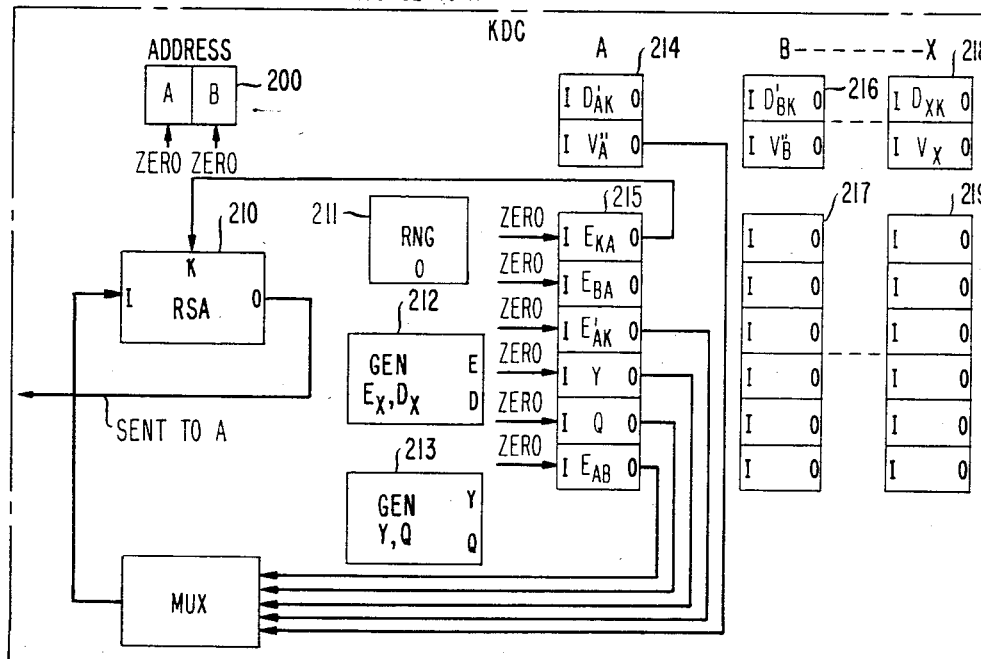
*FIG. 27* COMPUTATION OF MESSAGE TO A

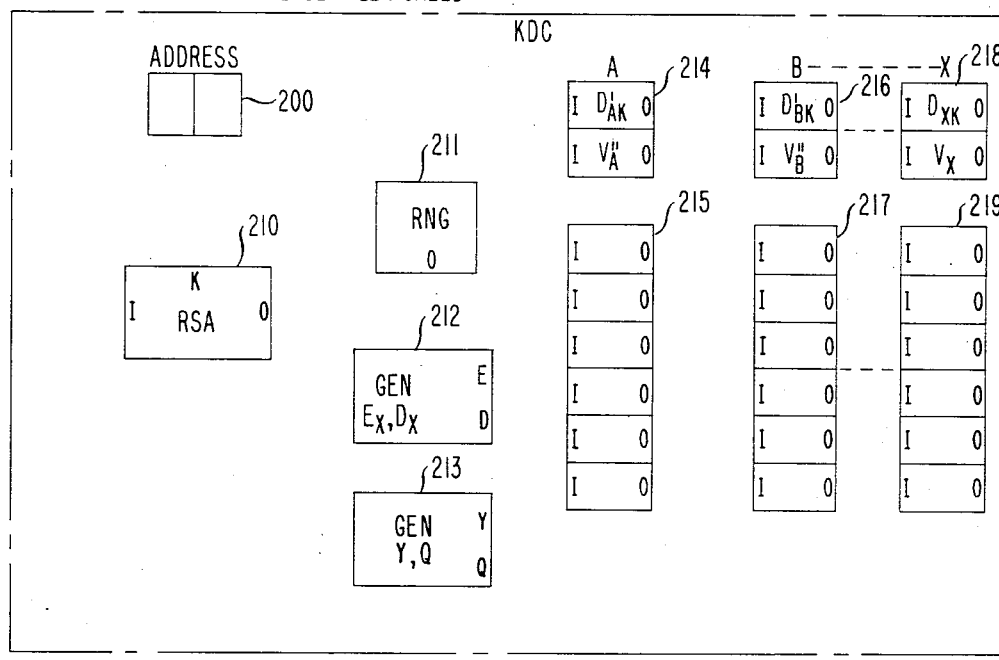
FIG. 28 IDLE STATE BETWEEN CALLS

ENCRYPTION SYSTEM KEY DISTRIBUTION METHOD AND APPARATUS

BACKGROUND OF THE INVENTION

This invention relates to the establishment and distribution of cipher keys in a cryptographic system.

Cryptographic systems are now gaining favor, both for voice as well as data transmission. In such systems it is typically necessary that the parties to a particular transmission each have cryptographic keys to encrypt and decrypt the cipher transmissions. It follows that a compromise to a cryptographic key will in turn reduce the security of subsequent transmissions involving that key. Thus, great precautions must be taken to distribute the cryptographic keys among the system users. Such distribution, for example, using secure couriers to manually update the keys may be possible when the community of users is priorly known but becomes increasingly more difficult when either the number of parties is large or parties who seldom communicate with each other wish to do so. The responsibility for keeping the cryptographic key secure after distribution rests with each user and the longer the key remains effective the greater the risk of it becoming compromised.

Thus, from a practical point of view it is desirable to have the cryptographic key effective for a single session, requiring a new key for each new session. When couriers are used, however, this becomes costly and time consuming, especially when a party wishes to place many secure calls or have many secure sessions.

Attempts have been made to electronically distribute cryptographic keys between users from a key distribution center. One such example is shown in Rosenblum U.S. Pat. No. 4,182,933, issued Jan. 8, 1980. While such attempts have found some degree of success they all suffer from the problem that they are subject to compromise because they usually rely on the security of the transmission media between the key distribution center and the terminal for the distribution of session key information. Thus, an intruder need only compromise the key distribution channel to obtain subsequent session keys. Elaborate systems have sometimes been established to detect such a compromise, all of which are either costly or minimally effective.

Another problem with key distribution centers is that the center can derive the information used to decrypt the secure data exchange between users and thus could theoretically monitor the secure session transmission.

SUMMARY OF THE INVENTION

We have solved the above-identified problems by arranging a key distribution center (KDC) which communicates over a channel with the individual terminals. The channel, or data link, can be a dial-up telephone line, a packet-switched data network, dedicated lines, or other communications channel types, over which secure communication is possible. The terminals operate in conjunction with the KDC to establish a session key for secure transmission between two or more terminals. The session key at a terminal is constructed from information generated at that terminal in conjunction with information communicated from the KDC and is known fully only to the terminals involved in the session and not to the KDC. Thus, when two terminals have established a session key, they may securely communicate with each other for the duration of that session.

At the conclusuions of the secure data exchange, the session keys should be destroyed, and when either station wishes to establish additional secure communication either between themselves or to other stations, a new session key will be established in cooperation with the KDC.

Both the terminal-KDC channel and the KDC-terminal channel, as mentioned above, are secure links in that they are protected by cryptographic key information which is unique to each terminal and to the KDC on a one-call-only basis. Accordingly, whenever a connection is established between a terminal and the KDC, each has information previously stored, referred to as terminal-unique key information, and this priorly stored information is used to establish both new KDC-terminal link keys, referred to as call-setup key information, and new session key information. During the establishment of the session keys, the terminal and the KDC each modify their respective terminal-unique key information so that on a next call between the KDC and the same terminal, this new key information must be used in order to establish a secure communication path. The precise manner in which this happens will be discussed hereinafter. In this manner, an intruder on the key distribution between a terminal and the KDC must be adding and substituting information on the channel from the beginning and must stay on the channel throughout several calls, since once the intruder leaves it is possible to detect, at least by hindsight, that a compromise has occurred. This is a result of the fact that the intruder is substituting random information that may be monitored.

One aspect of our system is that an intruder, in order to obtain useful information exchanged between two valid users of the system, may gain the terminal-unique information that is stored at the terminal, and he must also gain the terminal-unique information that is stored in the key distribution center for that specific terminal. The intruder then, on the very next key exchange involving that terminal and the key distributing center, must actively participate, i.e., substitute his own generated key information on that channel. Then the intruder must also substitute information on the channel between the two communicating terminals, and also must continue the above substitutions on the channels for an indefinite period of time or risk detection.

BRIEF DESCRIPTION OF THE DRAWING

These attributes of our invention, together with the operation and utilization of the invention in a specific embodiment, will be more fully apparent from the illustrative embodiment shown in conjunction with the drawing which:

FIGS. 6–9 show, in sequence, an implementation of the establishment of key information and control data within each terminal; and FIGS. 20-28 show, in sequence, an implementation of the establishment of key information and control data within the KDC. In this system we have a variety of terminals.

GENERAL DESCRIPTION

Figure 1:
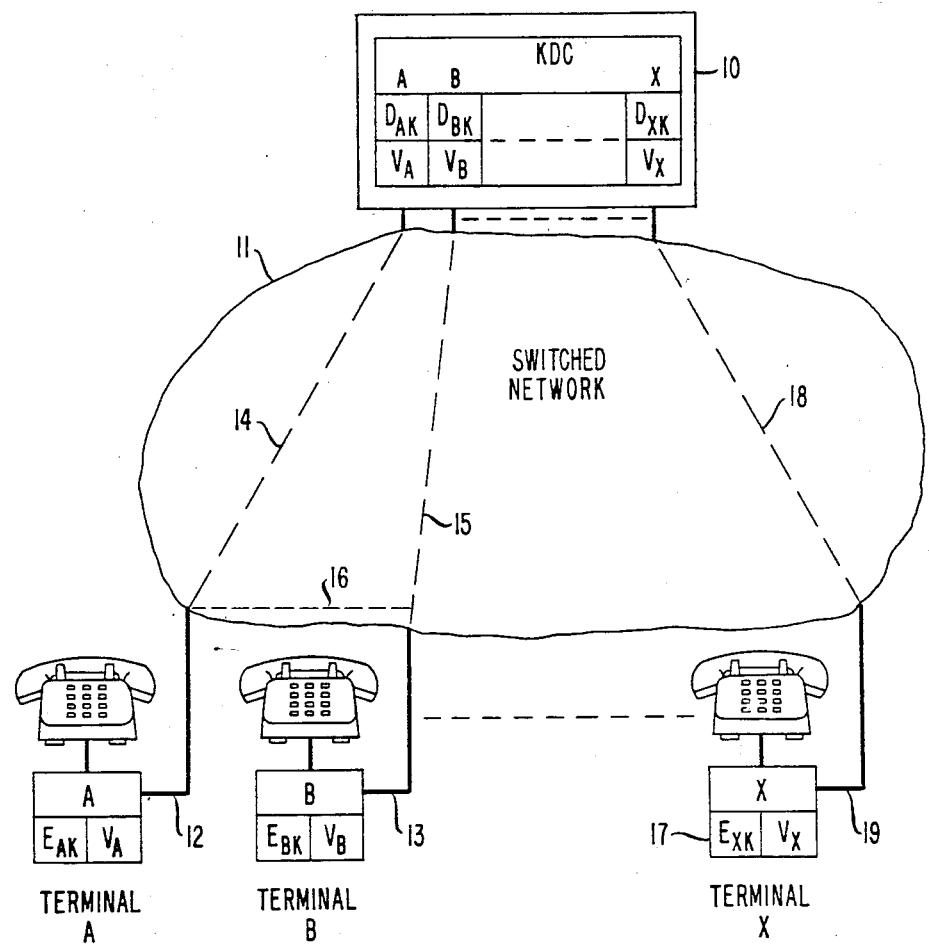
FIG. 1 shows an overall system using a KDC and several terminals.

FIG. 1 shows a number of terminals, A, B and X, connectable to each other and to KDC 10 via some transport network (e.g., public switched network). These terminals should be able to set up a secure channel between themselves in order to exchange secure information. In this process they must both communicate with the KDC. The transmission line 12 from terminal A is connected through link 16 to transmission line 13 to initiate a secure call to terminal B. Once the users decide to initiate a secure data exchange, each terminal sets up a transmission line, such as link 14 for terminal A, to the KDC.

An exchange of information will then occur from terminal A to the KDC and from terminal B to the KDC. Once the KDC has received both of these messages, it will formulate two distinct messages that will be sent respectively to terminal A via link 14 and to terminal B via link 15. These individual messages will contain session key information, as well as other pertinent information described below. This session key information has originated at terminal A and at terminal B and is exchanged through the KDC. Once the exchange has taken place between the two terminals and the KDC, link 14, which is the key distribution link between terminal A and the KDC, is then taken down, and key distribution link 15 between the KDC and terminal B is taken down. Link 16, which is the session link between terminals A and B, is re-established. Further key information is exchanged based on the prior partial exchanges so as to derive independently at both terminals the session key, and finally using that session key information, data (i.e., digital data or digital voice) can be transmitted in secure fashion on data link 16.

Since further session information was derived between terminals A and B independent of the KDC, a malicious operator of the KDC cannot derive the key information used to decrypt the secure messages sent between terminals A and B without actively substituting information on the session channel.

Also, at this point, as will be seen, contained within the messages that were sent between the KDC and the terminals was new terminal-unique key information to secure the next key distribution between the terminals of the KDC. This new information is independent of the previous information and therefore is unique to it.

DETAILED DESCRIPTION

Figure 2:
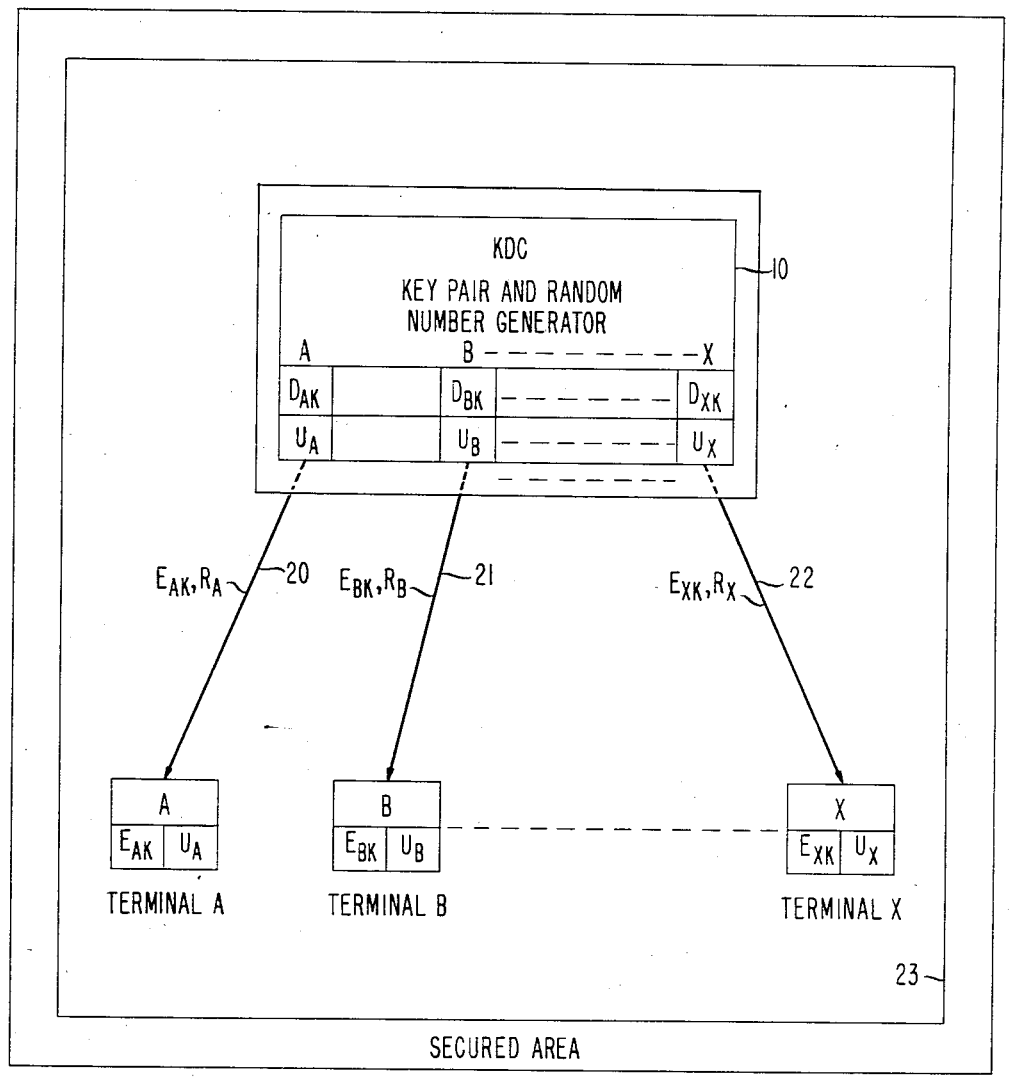
FIG. 2 shows an implementation of the initial establishment of information in both the KDC and the terminal within a secure area.

Turning now to FIG. 2 the initial setup between the terminal and the KDC must be made in an authentic manner such that the information transported to the terminals from the KDC is not modified. One implementation is where the transport is made within a secured area, such as secured area 23. Since subsequent communications between the KDC and each terminal depend upon the prior communication, it is important that at some period in time they both contain the proper information for start-up, and ideally this is done in the secured area so that there can be no breach of security.

On the initial system setup (based on the secured area implementation shown in FIG. 2) the terminals are brought within the secured area 23, and the KDC can generate terminal-unique key pairs for each terminal.

The exact function of these key pairs will be described later. The KDC will generate a terminal-unique decryption key for each terminal and the corresponding encryption key. This encryption key must be placed in the terminal-unique key storage for each terminal with the corresponding decryption key stored in the terminal-unique key storage at the KDC under the address of that terminal. In addition, a random number, Ua for terminal A, unique to each terminal is stored in the verification information storage at the KDC also at the address of this terminal. This same random number must be loaded and stored in the verification information storage in the terminals and will be used for a verification check on the first call setup to the KDC.

Figure 3:
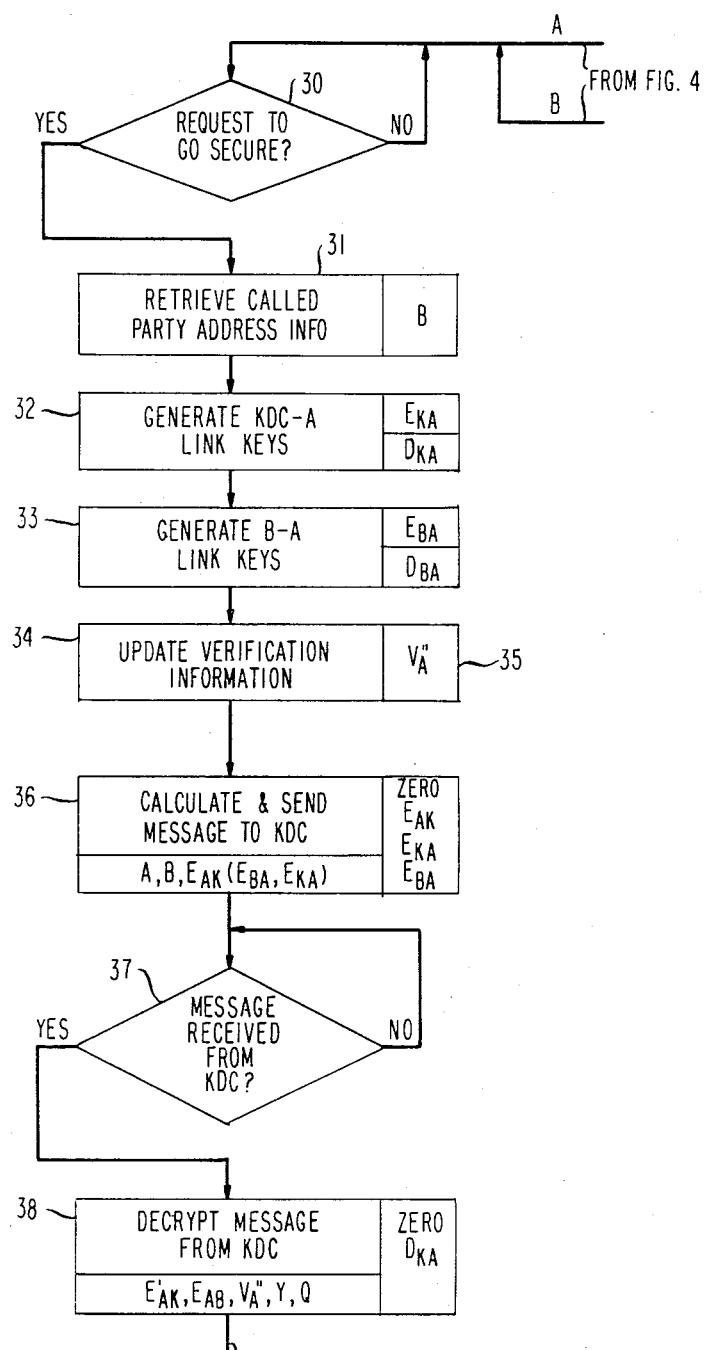
FIGS. 3 and 4 show a flow chart detailing what occurs within each terminal.
Figure 4:
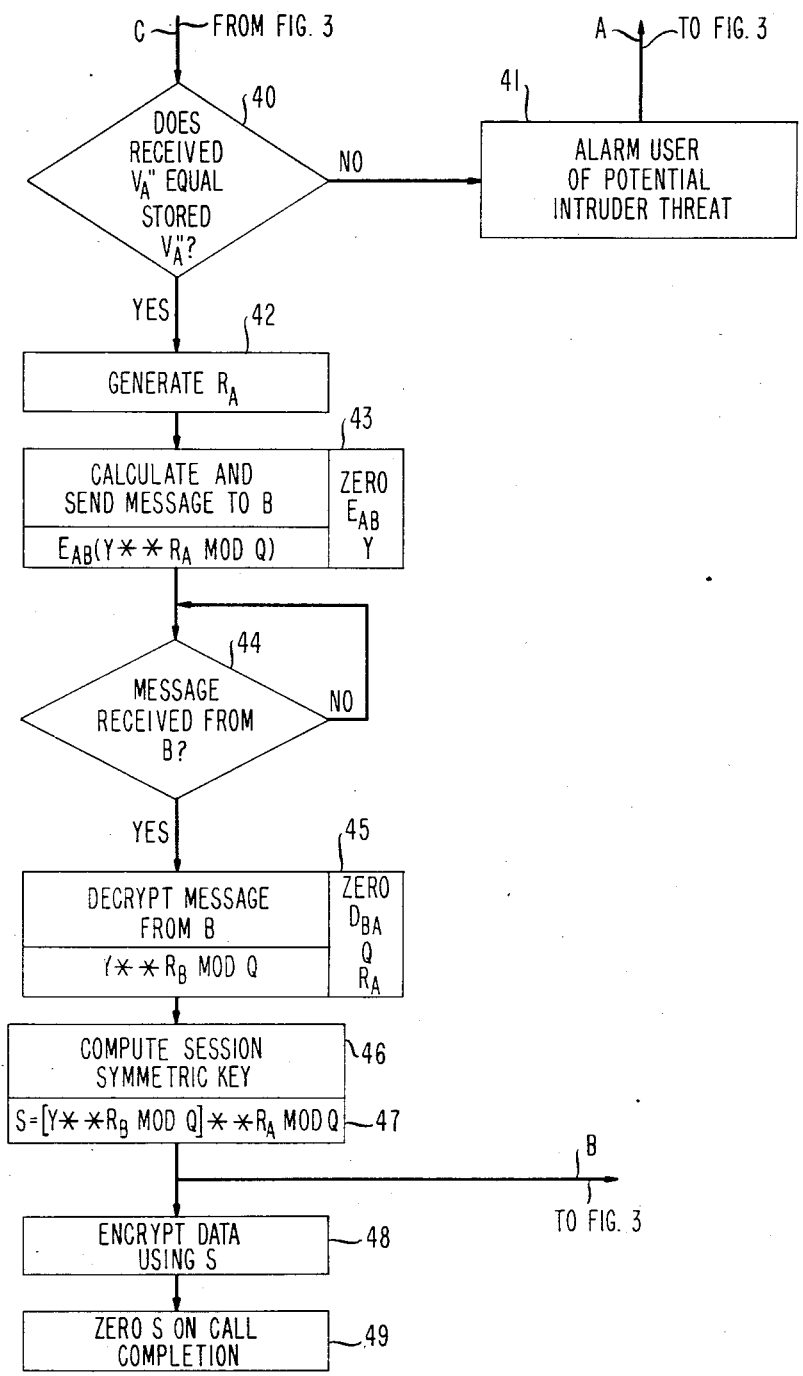

FIGS. 3 and 4 are flow charts representing the action that occurs within a terminal, for example, terminal A.

Figure 5:
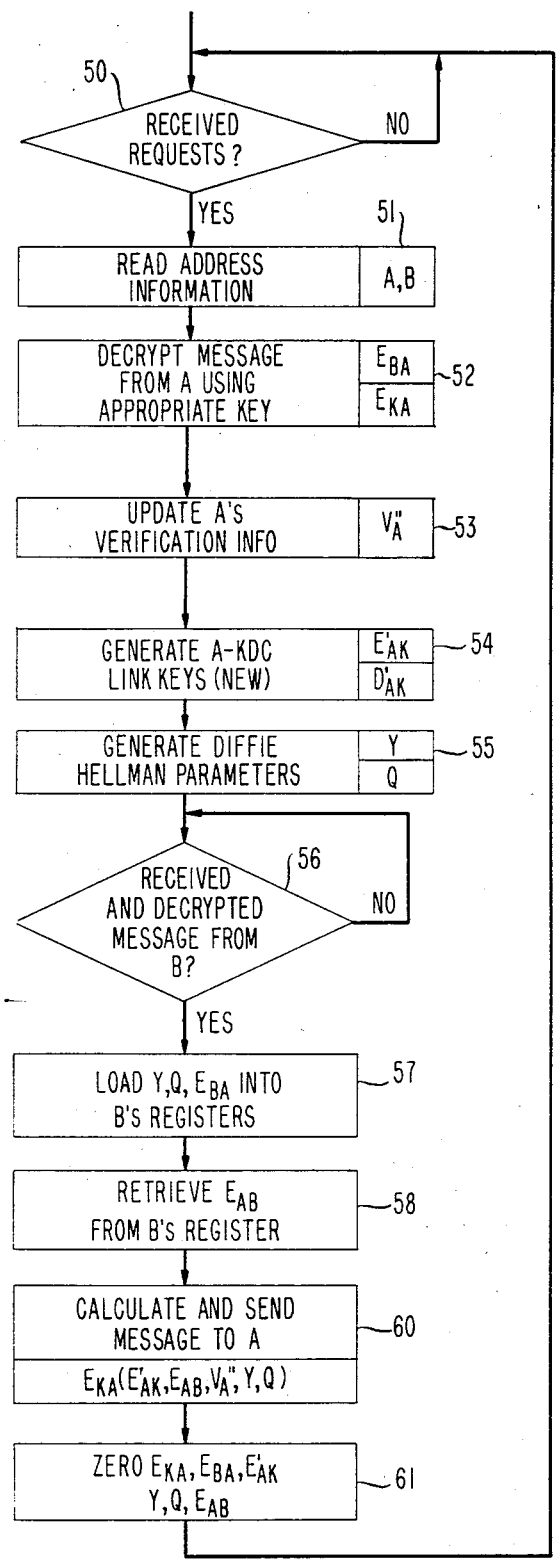
FIG. 5 shows a flow chart detailing what occurs within the KDC.

FIG. 5 is a flow chart representing what actions occur within the key distribution center.

The discussion which will follow is a discussion with respect to a time sequence between the terminal and the KDC to illustrate both how terminal-unique keys are updated, and how call-setup and session keys are distributed. This discussion will occur with respect to FIGS. 6 through 28. FIGS. 6 through 19 show the apparatus within the terminal and show on a step-by-step basis how the call-setup keys and the session keys are established. FIGS. 20 through 28 show the apparatus within the KDC, each figure showing a specific operational aspect of the establishment of the keys.

Turning now to FIG. 6 we will discuss the specific apparatus used in the terminals. The actual generation of the numbers will be discussed hereinafter. Apparatus 72 is a random number generator which is a device or algorithm that produces bits (zeros and ones) that are equally likely to occur. This generation may be based upon a noisy diode and any number of algorithms can be used to attain statistically independent output of 0's and 1's. The more equally likely these random number generators are, i.e., the more random this function is, the higher the security level will be. The output of the random number generator is a serial stream of zeroes and ones where the correlation between one or a group of bits is zero. The bidirectional asymmetric key generator, apparatus 73, takes as input a random number from random number generator 72 and will compute an encryption key and the matching decryption key such that the encryption key cannot be derived from the decryption key and vice versa. The generation of these keys as an example could be done in accordance with the RSA algorithm, as described by Rivest, Shamir, and Adleman in a paper entitled, "A Method for Obtaining Digital Signatures and Public Key Crypto Systems,38 which publication is hereby incorporated by reference, which appeared in CACM, Vol. 21, No. 2, February, 1978, on pages 120-126.

Apparatus 74 implements a bidirectional asymmetric cryptographic algorithm (e.g., the RSA algorithm) that is, a cryptographic algorithm based on two distinct keys where the encryption key cannot be derived from the decryption key and vice versa. Apparatus 74 has two inputs (I and K) and one output (O). The input I is the bits to be encrypted or decrypted. The input K is the key, either encryption or decryption (the RSA algorithm performs the same function regardless of encryption or decryption). The output will be the inputted bits encrypted or decrypted with the supplied key. This algorithm is also described in the aforementioned paper. Functionally, apparatus 75 is the embodiment of two functions f and g such that: given f(R, P) and P, one cannot determine R; g(R1, f(R2, P), P)=g(R2, f(R1, P), P); and given f(R1, P), f(R2, P), and P one cannot determine R1, R2, or g(R1, f(R2, P), P).

Apparatus 75 performs the above functions via, for example, the Diffie-Hellman algorithm, which is described in a paper by Diffie and Hellman entitled "New Directions in Cryptography," published by the *IEEE Transactions on Information Theory*, Vol. IP-22, November, 1976, on pages 644–655, which is hereby incorporated by reference. The input to this algorithm is a base Y, a modulus Q and an exponent EXP. The output is Y raised to the EXP power modulus the Q. The functions f and g are the same as discussed above in this example.

The storage requirements are depicted by registers 71, 70 and 76. These are the semi-permanent register 71 which contains both the verification information Va and the terminal-unique key information Eak used to encrypt messages to the KDC. Temporary register 70 can be in any state initially and is used during the interaction with the KDC on a secure call setup. The address register permanently contains the address (i.e., a public piece of information that uniquely identifies A to the KDC) of the terminal (terminal A in this case) where it is located. During a secure session (or call) setup, the address register will also contain the address of the terminal which is being called. The registers containing verification information and encryption and decryption information may vary in size depending upon the specific algorithm used but in this example should be on the order of 1,000 bits each. Information pertaining to the symmetric session key and the random number should be on the order of 100 bits, and the address information will be dependent upon a terminal numbering plan both unique and known to the KDC. For example, it could be the telephone number of the specific terminal or it could be the serial number of the terminal.

Turning to FIG. 20 we will now discuss the working of the modules within the key distribution unit. The address register at the KDC, register 200, performs the same function as the address register at the terminal. The RSA function at the KDC, apparatus 210, performs the same function as the RSA function at the terminal, as previously described. The random number generator, apparatus 211, performs the same function as the random number generator at the terminal previously mentioned. The generator of the encryption and decryption keys apparatus 212 has the same function as described previously in the terminal. Apparatus 213 is a generator of the parameters used as inputs to the apparatus 75 described previously. For this particular example these parameters are the base and modulus for the Diffie-Hellman algorithm. It requires as input the output of the random number generator, apparatus 211. The method of generation is described in the aforementioned paper by Diffie.

There is a semi-permanent storage at the KDC, registers 214 and 216, which stores verification information Va and terminal-unique decryption key information Dak between calls. Semi-permanent registers 215 and 217 are used to store information during the call setup progress. These registers have the same functions as described previously for the terminal.

System Operation

The operation of the system will now be explained beginning with FIG. 3. Initially the key management equipment in the terminal will be in the wait state until a request is received from the terminal controller processor to initiate a secure call. At this point, as discussed, there is stored in the terminal the terminal-unique encryption key that will be used to encrypt information that is sent to the KDC. Also stored is the verification information. These two pieces of information were stored from the last call (or from the initial setup) that was made by this terminal. This is shown in FIG. 6 as Va and Eak.

Once a request is received to initiate a secure call, the address of the called party must be given to the key management equipment via the controller processor. This is seen in FIG. 3, box 31. At this point, there are generated new call-setup keys. This is shown in box 32 and in FIG. 7 as Eka and Dka. In box 33 there is shown the generation of partial session keys that will be used to encrypt data on the link from terminal B to terminal A. This is shown in FIG. 8 as Eba and Dba.

At this point, the verification information is updated using the keys that were just generated. The update function is specified as follows:

$$Va1' = f(Va1, E1) \text{ and } Va2' = f(Va2, E2)$$

where ' denotes updated and Va1Va2=Va. Va is the stored verification information and the E's are the just-generated encryption keys. The properties of f are as follows:

(1) for every V, E1, E2: $f(V, E1) \neq f(V, E2)$ where $E1 \neq E2$;

(2) for every V21, V2, E: $f(V1, E) \neq f(V2, E)$ where $V1 \neq V2$;

(3) given V and $V' \neq f(V, E)$ it is difficult to determine E; and (4) in the case where E is an asymmetric encryption key, D cannot be determined from E.

For this example, Va′=Va1′|Va2′ where Va=Va1|Va2, Va1′ is equal to Va1 encrypted with Eka, and Va2′ is equal to Va2 encrypted with Eba. This update process is depicted in FIG. 9. The first half of the verification information Va1 is read from storage and provided as an input to the RSA algorithm. The key that is used to encrypt this information is the call-setup key, Eka, that was just generated. This becomes Va1′ and overwrites Va1 as seen in FIG. 10. Next, the second half of the verification information Va2 is encrypted using Eba just generated. The result Va2′ overwrites Va2 in the storage register. This is shown in FIG. 3, box 34, and in summary, the updated verification information Va″ is the verification information stored from the previous call, or given to the terminal on the initial setup from the KDC, where half is encrypted using the encryption part of the partial session key generated on this call and the other half is encrypted using the call-setup key for that call.

At this point, as shown in box 36, FIG. 3, and in FIG. 11, the message can be formatted to the KDC. The contents of this message are the encryption parts of the two keys that were just generated. Both the partial session key to be established between terminal A and B, Eba, and the new call-setup key Eka are encrypted using the terminal-unique encryption key Eak stored from the previous call from the KDC to the terminal or given to the terminal on the initial setup. At this point, the information that can be destroyed from the terminal is the terminal-unique encryption key, Eak, stored at the terminal from the previous call, and both the call-setup encryption key, Eka, and the partial session encryption key, Eba, that were generated by the terminal. The encrypted message is then appended to the address, A, of the originating terminal followed by the address, B, of the called terminal. This message is now sent to the KDC.

The terminal now will enter a wait state waiting for the information to be received from the KDC. This is depicted in box 37 of FIG. 3.

As shown in FIG. 5, the KDC will be in a wait state until a message is received from terminal A. This is shown in FIG. 5, box 50. Once the message is received, the KDC reads the address information within the message into the address register which gives it the index of the decryption key that must be used to decrypt the message. The KDC has in its storage from the previous call the matching verification information for each terminal and the terminal-unique decryption key for each terminal. This is depicted in FIG. 20, boxes 214 and 216.

The message from terminal A is decrypted using the terminal-unique decryption key corresponding to that terminal, Dak. The keys, both the new call setup key Eka and the partial session key Eba (to be distributed to terminal B) is temporarily stored in the KDC memory as depicted in FIG. 21.

At this point, as shown in FIG. 21, the KDC can update its verification information in the exact same manner as the terminal. This is done by encrypting each half of the stored verification information Va with the received session key information Eba and the received call-setup key information Eka, shown in FIG. 23. This produces the update verification information Va".

The key distribution center, as shown in FIG. 24, will now generate a bidirectional asymmetric encryption/decryption key pair, Eak', Dak'. The primes denote updated information. Eak' will be distributed to terminal A to be used on the next call setup to the key distribution center. The decryption key Dak' overwrites the decryption key Dak that was stored from the previous call.

Two other pieces of information are also generated at this time. These are the parameters that will be used by the terminals to create symmetric session keys; in this case they are the parameters of the Diffie-Hellman algorithm. One is the base Y and the other is the modulus Q as previously described. Functionally, the amount of information that is generated at the KDC and sent to each terminal may vary depending upon the precise algorithm. This information is stored in temporary storage and will be used as part of the message sent back to both terminal A and terminal B. This generation process is depicted in FIG. 25 and refers to the flow chart box 55, FIG. 5. By this point, as shown in FIG. 26, the KDC must have received a message from terminal B in order to complete the call to terminal A. If not, the KDC process for terminal A must wait until the process for terminal B has reached this point. This is so it can give terminal A the partial session key information Eab generated at terminal B and also to be able to give terminal B the partial session key Eba generated at terminal A. Coordination between the processes must take place so that the same parameters generated by one process overwrites the parameters generated by the other process. This insures that the parameters sent to the terminals for the purpose of generating symmetric session keys are the same.

Once the internal exchange is made between the A registers and the B registers to coordinate the information inside the key distribution center, the messages can now be formatted for the terminals. This is shown in FIG. 27. The message to terminal A will consist of the new terminal-unique key information Eak' that will be used on a subsequent call to the KDC. It will also consist of the partial session key information Eab which it received from terminal B. It will also consist of the verification information Va" or a known reduction of Va" in terms of the number of bits. It will also consist of the base Y and the modulus Q of the Diffie-Hellman algorithm. These five pieces of information will be encrypted using the call-setup key Eka received in the message from terminal A. The KDC destroys Eka, Eba, Eak', Y, and Q corresponding to terminal A and destroys Ekb, Eab, Ebk', Y, and Q corresponding to terminal B. The KDC will then send this output message back to terminal A. An analogous encrypted message is sent from the KDC to terminal B. At this point the KDC is finished with its processing.

FIG. 28 shows the configuration of the KDC after the call to terminal A has been dropped. The KDC has updated verification information Va" and updated terminal-unique decrypt key information Dak' which will be used on a subsequent call between terminal A and the KDC.

Referring back to the flow chart, FIG. 3, for terminal A, the key management equipment at the terminal has been in a wait state while the KDC has been functioning. FIG. 12 shows the key information stored at the terminal during this wait state. It is the updated verification Va" information and both decrypt keys Dka and Dba corresponding to the previously generated encryption keys.

FIG. 13 shows how the information received from the KDC is used in accordance with the box 38, FIG. 3. The call-setup decryption key Dka is used to decrypt the message received from the KDC. The five values (previously discussed) sent from the KDC are now used in the following way. The first piece of information is the new distribution key Eak' that is stored in the semipermanent register 71 and will be used on a following call made from this terminal to the KDC. It is the updated terminal-unique encryption key. The second piece of information is the partial session key Eab which was generated at B and sent through the KDC to terminal A. The third piece of information is the updated verification information Va", which can now be compared with the verification information stored at terminal A. The fourth and fifth pieces of information are the parameters to the Diffie-Hellman algorithm, the base Y and the modulus Q, which terminal A stores in temporary storage.

Referring to FIG. 4, box 40, at this point the terminal will compare the verification information it received from the KDC and either the verification information which is presently stored or some known reduction of that verification information—FIG. 14. If this matches, then the process will continue as normal. If this does not match, an alarm could be given to the terminal controller processor of a potential intruder threat on a previous call.

Assuming a success of the compared verification, the terminal can now take down the channel to the KDC and establish a channel to terminal B, if not already established. At this point, terminal A and terminal B can communicate data securely using the asymmetric session keys Eab and Eba. If a symmetric session key is needed, the following steps can be taken. The calculation of the message to be sent to terminal B is shown in FIG. 15. First, the base Y and modulus Q of the Diffie-Hellman algorithm are used along with a random number Ra generated by the random number generator 72. These inputs are given to the Diffie-Hellman algorithm 75 and the output is then an input to the RSA function 73. The random number Ra is also stored in temporary storage. Eab is used as the key to the RSA function 73. At this point the session key information Eab received from terminal B and the base number Y may be destroyed. The output of the RSA algorithm is sent to terminal B.

Terminal A' key management equipment will now enter a wait state shown in FIG. 4, box 44, waiting for a message to be returned from terminal B. The idle state is depicted in FIG. 16 and in storage is the decrypt session key Dab which terminal A generated, the modulus Q of the Diffie-Hellman algorithm generated by the KDC and the random Ra number that was generated by terminal A.

As shown in FIG. 17, upon receipt of the message from terminal B, terminal A will decrypt the message using its decryption key Dba stored from the initial generation of the partial session key. Dba can now be destroyed. The output of this will be fed into the Diffie-Hellman algorithm as the base. The exponent will be the random number Ra which was priorly generated and the modulus Q is also input into the algorithm. The output of the Diffie-Hellman algorithm will be symmetric session key information which will equal the session key information that terminal B has calculated. Q and Ra can now be destroyed.

At this point, terminals A and B have established symmetric session key information between themselves that is not derivable by the KDC. This key information may be used in a symmetric key algorithm like the Data Encryption Standard (DES) to encrypt data. What is stored now in the terminal until the next request for a secure session (or call), as shown in FIG. 18, is the updated verification information Va" and the terminal-unique key Eak' which it received from the KDC to be used to encrypt the next message to the KDC.

It should be noted that the actual generation of the desired data at the terminal and at the KDC is operative under control of a computer processor and is programmed in accordance with the flow charts shown in FIGS. 3-5 to perform the sequence of data transfers detailed herein. Such a processor, while not shown, can be any one of several well-known microprocessors, such as for example, the Intel 8086 microprocessor, working in conjunction with the terminal and KDC apparatus shown and detailed herein above.

It should also, be noted that one skilled in the art could use different encryption algorithms and different equipments to achieve the same results disclosed herein without departing from the spirit and scope of our invention.

What is claimed is:

1. A key distribution method for communicating cipher keys between two terminals via a key distribution center, KDC, said method comprising establishing between any one terminal and said key distribution center a terminal-unique cipher key for controlling the generating of session keys, cooperating by transmitting information using said established terminal-unique cipher key between said KDC and said one terminal on a subsequent connection between said KDC and said one terminal to establish a session key for use by said one terminal in a subsequent secure transmission between said one terminal and a second terminal, and changing said priorly established terminal-unique cipher key in response to use of said priorly established terminal-unique cipher key on said subsequent connection between said one terminal and said KDC.

2. The invention set forth in claim 1 wherein said session key is generated from the asymmetric exchange of information between said one terminal and said KDC plus the subsequent exchange of information between said first and second terminals.

3. The invention set forth in claim 2 wherein said session key at said one terminal is random with respect to information at said KDC.

4. The invention set forth in claim 2 wherein said session key at said one terminal is underivable with respect to any information at said KDC.

5. A key distribution center for controlling the dissemination of session cipher keys between remotely located terminals, said center arranged for switched access to a plurality of said terminals, said center comprising means for establishing communication cipher keys between said center and each said terminal having access thereto, each cipher key unique to each said terminal, means operative when said terminals access said center for bidirectional asymmetrically exchanging information with said accessing terminals using, as a foundation for said exchange, said priorly established communication cipher keys, and means responsive to said exchanged information between said center and two of said terminals and the subsequent bidirectional asymmetrical exchange of information between said two terminals for allowing said two terminals to establish a session cipher key for secure transmission between said two terminals.

6. The invention set forth in claim 5 wherein said key distribution center further comprising means for changing said established communication cipher keys as a result of said exchanged information.

7. The invention set forth in claim 5 wherein said cipher key establishing means uses information from a prior transmission from a particular terminal for establishing said cipher keys to said particular terminal.

8. The invention set forth in claim 5 wherein said exchanged information includes information generated in part at said center for the random generation of said session key allowing said session key to be underivable with respect to any information at said center.

9. A key distribution center for controlling the distribution of cipher control information among a number of terminals, said center comprising means for individually exchanging encoded information between any of said terminals, said exchange for any particular terminal based partially upon a last information exchange between said particular terminal and said center, means for identifying at least two terminals where encrypted session information is to be exchanged and for accepting from said identified terminals certain encryption control information, and means for modifying, according to a preestablished pattern, accepted information from said identified terminals and for communicating said modified information to the other of said terminals so as to allow each of said terminals to thereafter establish, independent of any information available at said center, a cipher key allowing said session information to be encrypted.

10. An encryption terminal operable for communicating with other said terminals for the exchange of encrypted information, said encryption occurring under control of a session encryption key, said terminal including
- means for establishing between said terminal and a key distribution center a unique cipher key for exchanging information between said terminal and said center,
- means for storing information pertaining to established exchanged cipher keys with said center,
- means for comparing said stored information against information received from said center during an information exchange for verifying that the information on the last exchange to said center was not modified, and
- session means for enabling a secure transmission with a selected other terminal, said session means controlled in part by said accepted exchanged information.

11. The invention set forth in claim 10 wherein said terminal also includes means for modifying said unique cipher key after each said information exchange with said center.

12. The invention set forth in claim 10 wherein said exchanged cipher keys are based, in part, on a bidirectional asymmetric information exchange with said center.

13. The invention set forth in claim 10 wherein said session means includes the establishment of symmetric session keys with said selected other terminal, said session keys derived by information from said center, said terminal and said other terminal.

14. An encryption terminal operable for communicating with other said terminals for the exchange of encrypted information, said encryption occurring under control of a session encryption key, said terminal including
- means for establishing between said terminal and a key distribution center a unique cipher key for exchanging information between said terminal and said center,
- means for storing information pertaining to established exchanged cipher keys with said center,
- means for exchanging information with said center, said information exchange enabled by said stored cipher key information,
- session means for enabling a secure transmission with a selected other terminal, said session means controlled in part by said information exchange, and
- means for modifying said unique cipher key after each said information exchange with said center.

15. The invention set forth in claim 14 wherein said exchanged cipher keys are based, in part, on a bidirectional asymmetric information exchange with said center.

16. The invention set forth in claim 14 wherein said session means includes the establishment of symmetric session keys with said selected other terminal, said session keys derived by information from said center, said terminal and said other terminal.

17. A cipher key distribution method for controlling the dissemination of session cipher keys between remotely located terminals and a key distribution center, said center arranged for switched access to a plurality of said terminals, said method comprising
- establishing pairs of communication cipher keys between said center and each said terminal having access thereto, each said pair being unique to each said terminal,
- exchanging, when one of said terminals accesses said center, information with said accessed terminal using, as a foundation for said exchange, said priorly established communication cipher key,
- communicating to said terminal, in response to said exchanged information, other information allowing said terminal to establish a session cipher key for use with an identified other terminal also having access to said center,
- said information exchanged between said center and said terminal includes receiving from said center the base Y and modulus Q of a Diffie-Hellman algorithm.

18. The invention set forth in claim 14 further including the step of modifying said communication cipher keys during each said information exchange.

* * * * *